US008242307B1

(12) United States Patent
Alabugin et al.

(10) Patent No.: US 8,242,307 B1
(45) Date of Patent: Aug. 14, 2012

(54) SITE-SPECIFIC CLEAVAGE OF NUCLEIC ACIDS BY PHOTOREACTIVE CONJUGATES

(75) Inventors: Igor V. Alabugin, Tallahassee, FL (US); Boris Breiner, Tallahassee, FL (US); Joerg C. Schlatterer, Tallahassee, FL (US); Serguei V. Kovalenko, Tallahassee, FL (US); Nancy L. Greenbaum, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 196 days.

(21) Appl. No.: 12/634,865

(22) Filed: Dec. 10, 2009

Related U.S. Application Data

(62) Division of application No. 11/615,037, filed on Dec. 22, 2006, now Pat. No. 7,695,912.

(60) Provisional application No. 60/753,156, filed on Dec. 22, 2005.

(51) Int. Cl.
*C07C 229/00* (2006.01)
(52) U.S. Cl. ...................................... 562/562
(58) Field of Classification Search .................. None
See application file for complete search history.

(56) References Cited

OTHER PUBLICATIONS

Mahon et al. Photosensitized DNA cleavage promoted by amino acids. Chem. Comm. (2003) published online, pp. 1956-1957.*
Patra et al. Red-light photosensitized cleavage of DNA by (L-lysine)(phenanthroline base)copper(II) complexes. Dalton Trans. (2005) published online, pp. 2798-2804.*
Gary Plourde II, Ahmed El-Shafey, Farid S. Fouad, Ajay S. Purohit, and Graham B. Jones, Protein Degradation with Photoactivated Enediyne-Amino Acid Conjugates, vol. 12, pp. 2985-2988, 2002.

* cited by examiner

*Primary Examiner* — Kenneth R. Horlick
*Assistant Examiner* — David Thomas
(74) *Attorney, Agent, or Firm* — Allen, Dyer, Doppelt, Milbrath & Gilchrist, P.A.

(57) ABSTRACT

A process of forming a double strand cleavage in DNA includes providing a reaction mixture containing double stranded DNA having a break in a first strand defining a target site in a second strand. The method continues by adding to the reaction mixture a photoreactive lysine conjugate selected from a lysine-enediyne conjugate, a lysine-acetylene conjugate or a combination thereof, for a time sufficient for the lysine conjugate to bind to the DNA adjacent the target site. The reaction mixture is then irradiated with electromagnetic radiation sufficient to photoactivate the lysine conjugate to cleave the second strand adjacent the target site.

4 Claims, 14 Drawing Sheets

SITE-SPECIFIC CLEAVAGE OF NUCLEIC ACIDS BY PHOTOREACTIVE CONJUGATES

RELATED APPLICATION

This is a divisional application of Ser. No. 11/615,037 filed on 22 Dec. 2006 and now U.S. Pat. No. 7,695,912 issued on 13 Apr. 2010, and which claimed priority from provisional application Ser. No. 60/753,156, which was filed on Dec. 22, 2005, all of which are incorporated herein by reference in their entirety.

FIELD OF THE INVENTION

This invention relates to biochemical methods and, more specifically, to a method for achieving efficient cleavage of double stranded DNA or site-selective cleavage of single stranded nucleotides.

BACKGROUND OF THE INVENTION

Restriction enzyme and siRNA technologies exist for site-specific knockout of genes. These two technologies are limited to one kind of targeted molecule. The presently described system is more flexible and provides an alternative method for directing the site-specific modification of nucleic acids, particularly DNA.

Aside from the common double helix, DNA forms a wide range of structural motifs, such as hairpin loops, triplex, tetraplex, bulged structures, as well as nicks and gaps. The individual structural features of these motifs make them potential candidates for specific targeting. Among these structural elements, nicks and gaps are promising for the development of sequence-specific DNA cleavage, since they already feature a break in the phosphate backbone of DNA.

Cleavage of the phosphate backbone of DNA can be caused by chemical reagents such as radicals and by radiation damage. In order to survive, cells developed enzymatic mechanisms for the repair which work efficiently on single strand (ss) damage. Any further cleavage on the opposite strand at the damage site leads to double stranded (ds) cleavage, which is hard to repair. Ds cleavage requires either a bifunctional reagent or detection and targeting of the damaged site. The only literature example of the latter is a complex natural antibiotic, bleomycin.

SUMMARY OF THE INVENTION

With the foregoing in mind, the present invention was directed to developing a general method for artificial and sequence-specific nucleic acid modification, based upon, but not limited to, our system. This ternary system is capable of targeting of nucleic acids. It comprises three elements:
  a DNA-sequence, providing recognition of the nucleic acid target, sequence selectivity;
  a terminal phosphate group on DNA-sequence, serving as a directing group for the ligand; and
  a phosphate detecting ligand (e.g., Lys, Arg, Ala, etc.)-warhead (e.g., enediyne, acetylene and other photoreactives) conjugate.

Our initial research efforts focused on the natural selectivity of lysine-enediyne conjugates towards a radioactively-labelled DNA oligomer. After irradiation in presence of lysine-enediyne conjugate and subsequent treatment with piperidine, we observed cleavage that is mostly localized at the Guanosine (G)-sites of the labelled DNA-strand. It is a known that oxidative damage (such as this case) is localized to G-sites, due to the lower oxidation potential of G compared to other nucleobases. Moreover, damage inflicted on sites other than G will tend to migrate ("hole hopping") to G over a distance of several nucleobases. A DNA-construct: 54mer with internal label near the 3' end, full-length counterstrand, is shown in FIG. 1.

These findings are summarized in the provisional application which is the parent to the present application and have been submitted for publication in a paper titled Internally Labelled Oligonucleotides: Investigation of Sequence Selectivity of DNA Photocleavage by Enediyne-, Fulvene-, and Acetylene-Lysine Conjugates, whose authors are Boris Breiner, Jorg C. Schlatterer, Serguei V. Kovalenko, Nancy L. Greenbaum, Igor V. Alabugin.

In a subsequent set of experiments, we tried to amplify the natural preference for cleavage at the G-sites; in particular, we placed phosphate groups on short, complementary counterstrands opposite to a GGG triad. Cleavage in these systems was clearly enhanced at the site opposite to the phosphate groups (the Gs in bold, as shown in FIG. 2). Cleavage at the other G-sites was not affected, i.e., the cleavage at the other G sites was as strong as it was in the experiments with a complete counterstrand.

As shown in FIG. 2, the DNA-constructs from left to right are as follows:
  a DNA oligomer with short counterstrand bearing a 5'-terminal phosphate group;
  a DNA oligomer with short counterstrand bearing a 5'-terminal phosphate group and a second counterstrand without a terminal phosphate group; all bases are base-paired; and
  a DNA oligomer with short counterstrand bearing a 5'-terminal phosphate group and a second counterstrand bearing a 3'-phosphate group; the second strand is shortened to leave a gap of 1 base between the two counterstrands.

In another set of experiments, the location of the phosphate group was moved to a site that was in-between two known G-cleavage sites. In these cases, cleavage was amplified at the two cleavage sites that were closest to the location of the phosphate(s) on the counterstrand(s).

As shown in FIG. 3, DNA-constructs from left to right are as follows:
  a DNA oligomer with short counterstrand bearing a 5'-terminal phosphate group;
  a DNA oligomer with short counterstrand bearing a 5'-terminal phosphate group and a second counterstrand without a terminal phosphate group; all bases are base-paired; and
  a DNA oligomer with short counterstrand bearing a 5'-terminal phosphate group and a second counterstrand bearing a 3'-phosphate group; the second strand is shortened to leave a gap of 1 base between the two counterstrands.

A conclusion drawn from these experiments is that it appears the ligand binds preferentially to the sites of the phosphate groups. The oxidative damage migrates (in part) away from this site, but the damage is clearly most prominent at the desired location.

The present invention, then, in general, includes the use of random ligand-warhead conjugates for site-specific damage of nucleic acids by complexation of phosphorylated, complementary RNA or DNA molecules. This method constitutes a new generation of site specific effects by bioactive compounds, an advantage being that all that is required to modify a known sequence of RNA or DNA is a short, complementary, phosphorylated DNA oligomer and a universal ligand attached to an active compound.

Therefore, the present invention advantageously provides that photoreactive conjugates, for example, lysine conjugates, can identify ss damage sites with high selectivity and induce DNA cleavage at the strand opposite to the damage site (as illustrated in Scheme 1). In Scheme 1, two components are potentially responsible for damage site recognition and subsequent cleavage: 1) formation of a hydrophobic pocket and 2) electrostatic interaction between the additional negative charges due to the presence of terminal phosphate moieties at the negatively charged DNA backbone ((−) signs) and the protonated amines of lysine moiety ((+) charges).

Use of this recognition for site-specific cleavage of single-stranded nucleotides can be achieved using the following sequence of steps. A. Annealing process that positions recognition site opposite the target at the original single strand oligonucleotide. B. Recognition of the target site by lysine conjugates. C. Sequence-selective photochemical conversion of single stranded DNA cleavage into double stranded cleavage.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may, however, be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Experimental Materials and Methods

The following description provides detailed instructions for carrying out the presently described invention and, particularly, all the experimental procedures employed.

General information: All reagents used were purchased from Sigma and Acros Organics if not otherwise noted. All buffers were prepared and pH-adjusted at room temperature (25° C.).

Irradiation conditions: Samples were placed on ice at a distance of 20 cm from 200 W Hg—Xe lamp (Spectra-Physics, Laser & Photonics Oriel Instruments with long pass filter with 324 nm cut-on wavelength).

Figure 1:
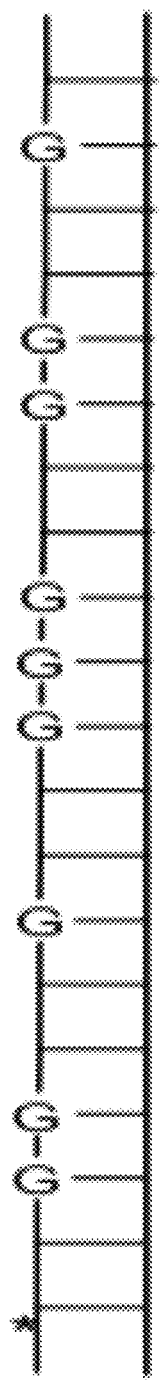
FIG. 1 is a diagram of a DNA-construct: 54mer with internal label near the 3' end, full-length counterstrand.
Figure 2:
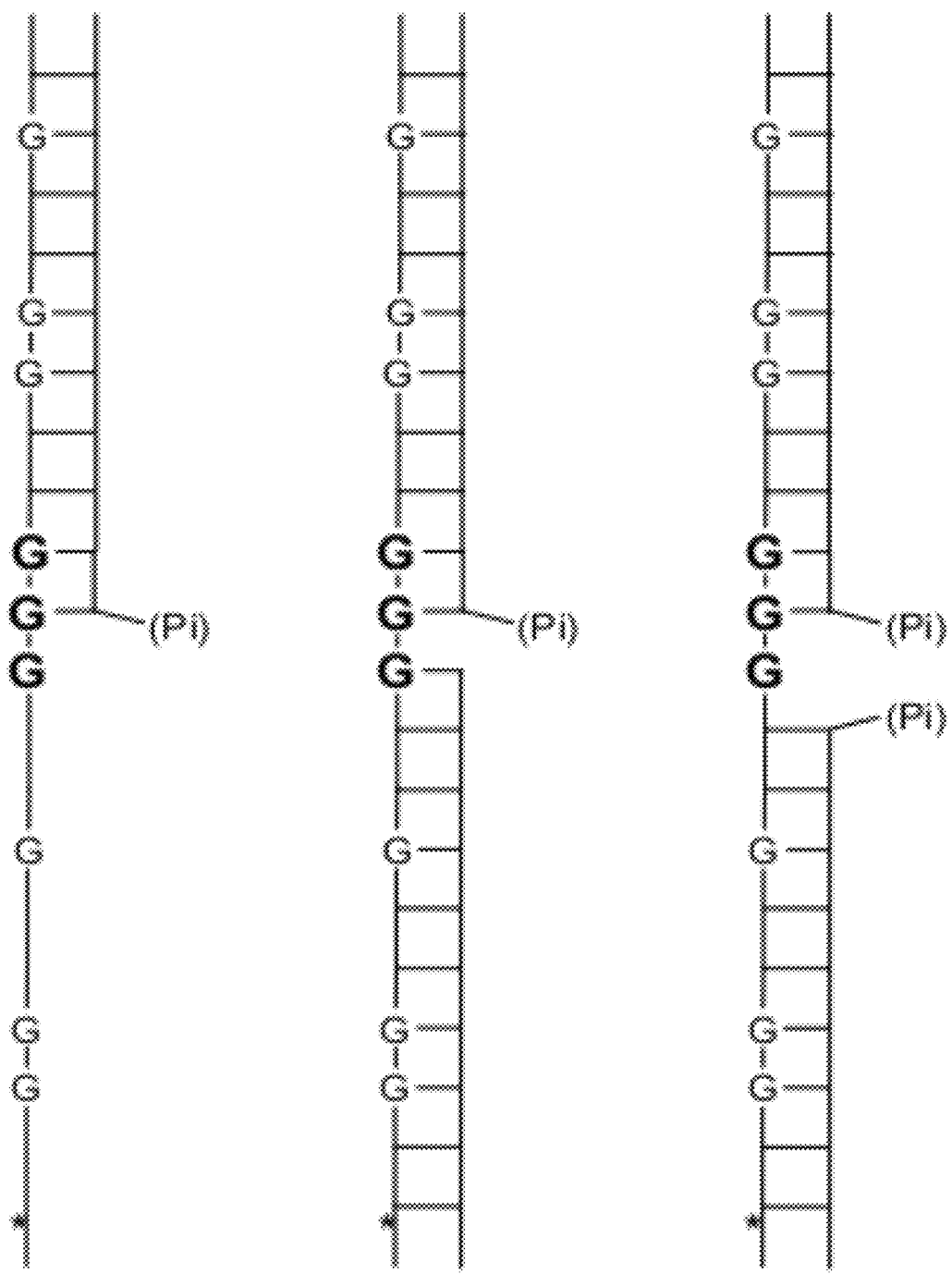
FIG. 2 shows DNA-constructs (from left to right): a DNA oligomer with short counterstrand bearing a 5'-terminal phosphate group; a DNA oligomer with short counterstrand bearing a 5'-terminal phosphate group and a second counterstrand without a terminal phosphate group (all bases are base-paired); and a DNA oligomer with short counterstrand bearing a 5'-terminal phosphate group and a second counterstrand bearing a 3'-phosphate group, wherein the second strand is shortened to leave a gap of 1 base between the two counterstrands.
Figure 3:
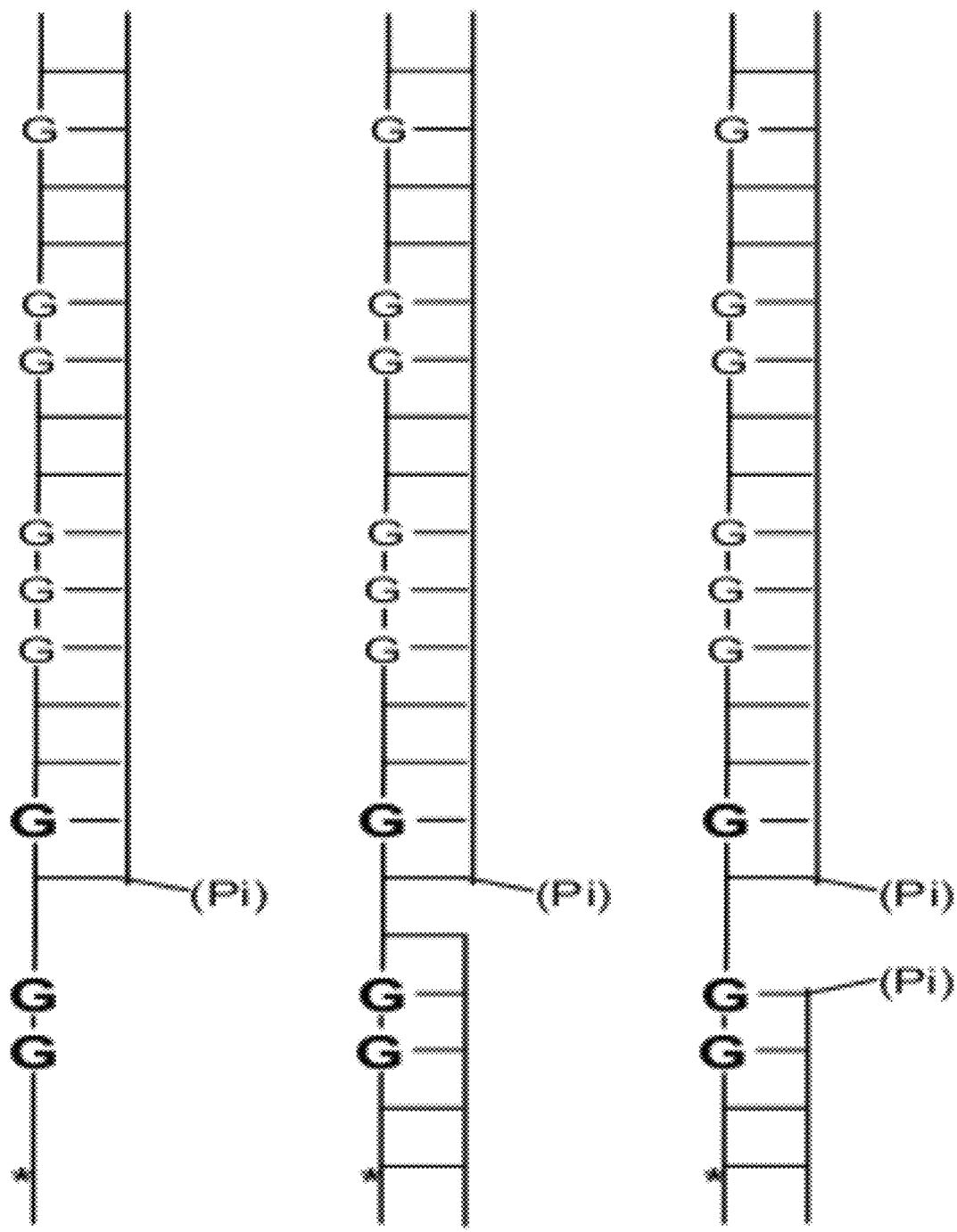
FIG. 3 shows DNA-constructs (from left to right): a DNA oligomer with short counterstrand bearing a 5'-terminal phosphate group; a DNA oligomer with short counterstrand bearing a 5'-terminal phosphate group and a second counterstrand without a terminal phosphate (all bases are base-paired); and a DNA oligomer with short counterstrand bearing a 5'-terminal phosphate group and a second counterstrand bearing a 3'-phosphate group, the second strand being shortened to leave a gap of 1 base between the two counterstrands.
Figure 4:
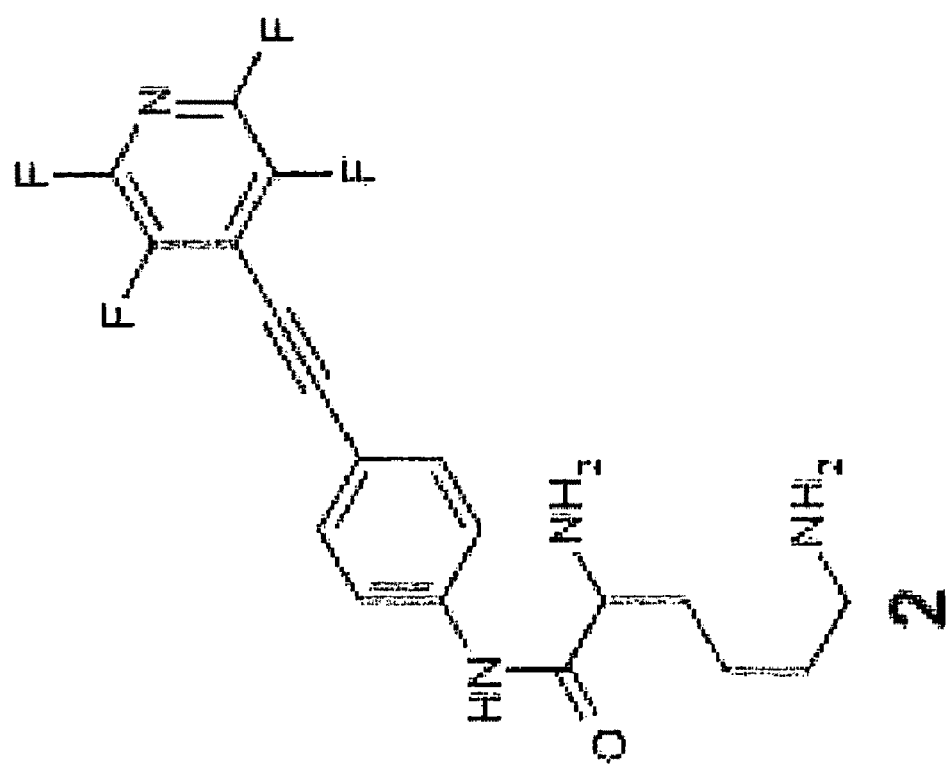
FIG. 4 provides the structures and formulas for two lysine conjugates referred to as formula 1 and formula 2; both shown as unprotonated amines.
Figure 4:
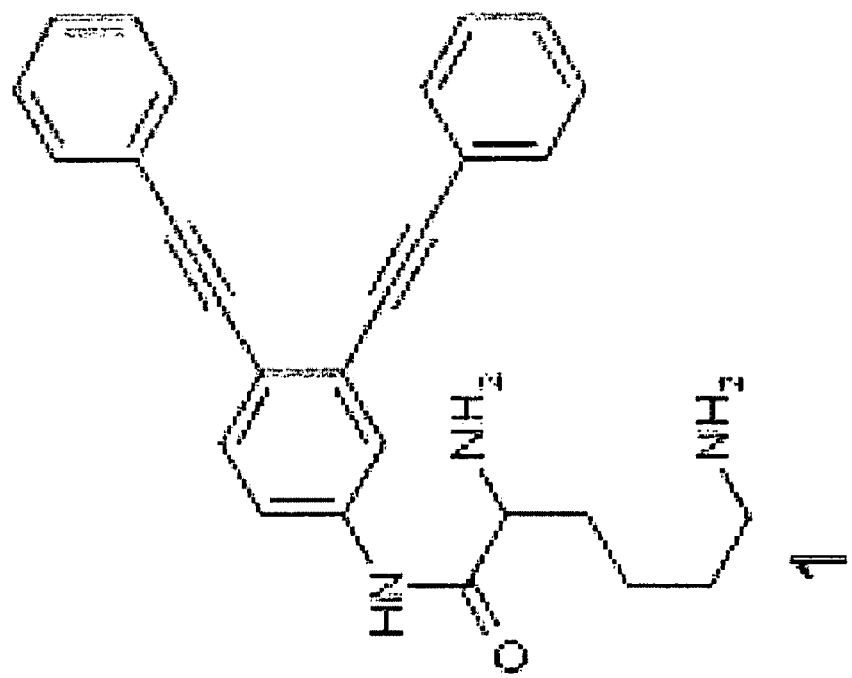

Lysine conjugates according to formulas 1 and 2 are shown in FIG. 4. The synthesis of compound 1 is described by Kovalenko, S. V. and I. V. Alabugin, Chem. Comm. 2005, 1444, a scientific paper which is accessible to the skilled and which is incorporated herein by reference in its entirety.

Figure 5:
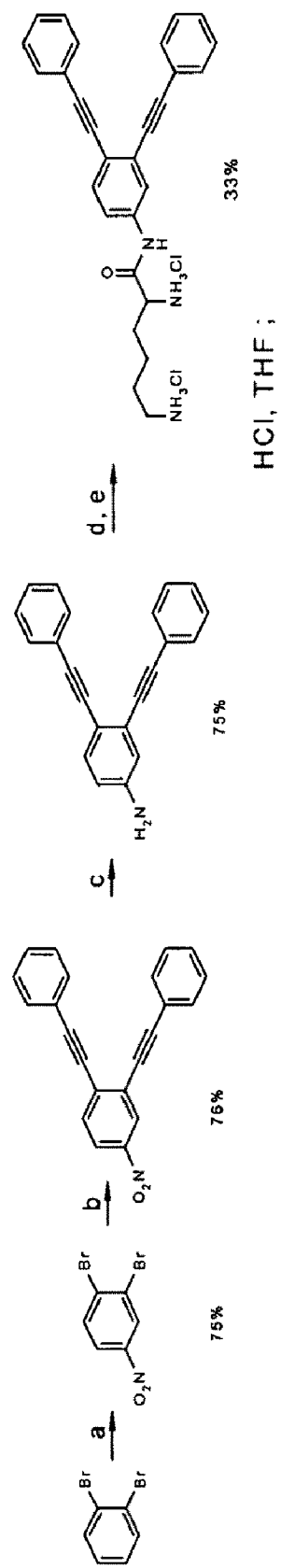
FIG. 5 depicts the method of synthesizing lysine-enediyne conjugate 1, wherein "a" is $HNO_3$, "b" is PhCCH, $PdCl_2(PPh_3)_2$, CuI, $(I—Pr)_2NH$, "c" is $SnCl_2$, HCl, THF, "d" is $Boc_2Lys(OH)$, $POCl_3$, Py, and "e" is HCl, THF.

Synthesis of lysine-acetylene conjugate 1: as Shown in FIG. 5

3,4-Bis(phenylethynyl)nitrobenzene

A mixture of 3,4-dibromonitrobenzene (4.2 g, 15 mmol), tris(triphenylphosphine)palladium chloride (0.5 g), and copper(I) iodide (0.15 g) in 70 ml of triethylamine was degassed by freeze/pump/thaw technique (three times). Phenylacetylene (3.4 g, 34 mmol) was added and the mixture was stirred at room temperature under nitrogen for 3 days. The amine was removed by rotary evaporation, and then the residue was dissolved in $CH_2Cl_2$ and washed with water. The organic layer was dried ($Na_2SO_4$), filtered, and rotary evaporated. Chromatography (EtOAc/hexanes, 1:30) gave enediyne (3.7 g, 76%) as yellow solid: mp. 97-98° C. $^1H$ NMR (300 MHz, $CDCl_3$) δ 8.42 (d, J=2.4 Hz, 1H), 8.16-8.12 (dd, J=2.4 Hz, J=8.4 Hz, 1H), 7.68 (d, J=8.4 Hz, 1H), 7.61-7.59 (m, 4H), 7.42-7.35 (m, 6H). $^{13}C$ NMR (68 MHz, $CDCl_3$) δ 146.6, 132.4, 132.0, 131.9, 131.8, 129.4, 129.2, 128.6, 127.2, 126.7, 126.6, 122.6, 122.3, 112.2, 98.8, 95.9, 87.0, 86.3. m/z (high res. EI) 323.0947 (Calc. $C_{22}H_{13}NO_2$ 323.0946).

3,4-Bis(phenylethynyl)phenylamine

A solution of 3,4-bis(phenylethynyl)nitrobenzene (2.5 g, 7.7 mmol), $SnCl_2$ (7.3 g, 39 mmol, 5 eq.), and HCl (5 mL, 10 eq.) in THF (20 mL) was stirred at room temperature for 5 h. After neutralization with NaOH (1.0N solution), product was extracted with dichloromethane. Solvent was evaporated and the residue was purified by column chromatography on silica gel using chloroform as the eluent to yield 1.7 g (75%) of 3,4-bis(phenylethynyl)phenylamine as a brown oil. $^1H$ NMR (300 MHz, $CDCl_3$) δ 7.67-7.61 (m, 4H), 7.42-7.35 (m, 7H), 6.85 (d, J=2.4 Hz, 1H), 6.62-6.58 (dd, J=2.4 Hz, J=8.4 Hz, 1H), 3.85 (broad, 1H). $^{13}C$ NMR (68 MHz, $CDCl_3$) δ 146.3, 132.9, 131.5, 131.2, 128.3, 128.2, 127.7, 126.5, 123.7, 123.1, 117.3, 117.2, 115.1, 114.9, 92.8, 91.2, 88.9, 88.5. m/z (high res. ESI) 294.1283 (Calc. $C_{22}H_{16}N$ 294.1283).

2,6-Diamino-hexanoic acid [3,4-bis(2,3,5,6-tetrafluoro-pyridin-4-ylethynyl)-phenyl]-amide Dichloride $Boc_2Lys(OH)$ (1.5 g, 5.1 mmol) and aniline (1.77 g, 5.1 mmol) were dissolved in pyridine (20 mL). The solution was cooled to −20° C. and phosphorus oxychloride (0.95 ml, 10.2 mmol) was added dropwise with vigorous stirring. The reaction mixture was stirred for 1 h at −20° C. and then at room temperature for 3 h. The reaction mixture was quenched with ice/water and anilide was extracted with $CH_2Cl_2$. The organic phase was washed with aqueous sodium bicarbonate, and saturated aqueous sodium chloride. The organic phase was dried with $Na_2SO_4$ and the solvent was evaporated in vacuo. The crude product was subjected to chromatography with $CH_2Cl_2/CH_3CN$ (10:1) as eluent and desired compound obtained as white solid (1.5 g, 47%): mp. 105-107° C. 1H NMR (300 MHz, $CDCl_3$) δ 9.16 (broad, 1H), 7.73 (s, 1H), 7.34-7.27 (m, 6H), 7.14-7.12 (m, 6H), 5.51 (m, 1H), 4.64 (broad, 1H), 4.2 (broad, 1H) 2.9 (m, 2H), 2.4 (s, 2H), 1.75 (m, 1H), 1.6 (m, 1H), 1.3 (20H). $^{13}C$ NMR (68 MHz, $CDCl_3$) δ 171.3, 156.3, 137.7, 132.2, 131.6, 131.5, 128.2, 128.1, 126.3, 123.3, 122.3, 122.2, 121.2, 119.1, 93.4, 92.8, 88.2, 88.1, 80.3, 79.1, 55.1, 39.6, 31.8, 29.5, 28.4, 22.6. m/z (high res. ESI) 644.3094 (Calc. $C_{38}H_{43}N_3O_5Na$ 644.3100).

Boc-Protected compound (1g) was dissolved in THF, and gaseous HCl was passed through that solution for 2 h. Then solvent was evaporated, and solid was washed with acetonitrile. After drying under vacuum the desired compound was obtained as yellow solid (0.47 g, 70%): mp. 295-297° C. (decomp.). 1H NMR (300 MHz, DMSO-d6) δ 8.4 (broad, 2H), 8.04 (s, 1H), 8.03 (broad, 1H) 7.78-7.76 (d, J=8.4 Hz, 1H), 7.65-7.62 (d, J=8.4 Hz, 1H), 7.60-7.40 (m, 10H), 4.14 (broad, 1H) 2.77 (m, 2H), 1.88 (m, 2H), 1.61 (m, 2H), 1.45 (m, 2H). $^{13}C$ NMR (68 MHz, CDCl3+CD3OD) δ 166.9, 136.9, 131.8, 131.1, 130.9, 128.1, 127.9, 125.9, 123.3, 122.6, 122.4, 122.1, 121.4, 119.2, 93.2, 92.7, 87.4, 87.3 53.1, 38.9, 30.5, 26.0, 28.4, 21.3. m/z (high res. ESI) 422.2223 (Calc. $C_{28}H_{28}N_3O$ 422.2232).

Figure 6:
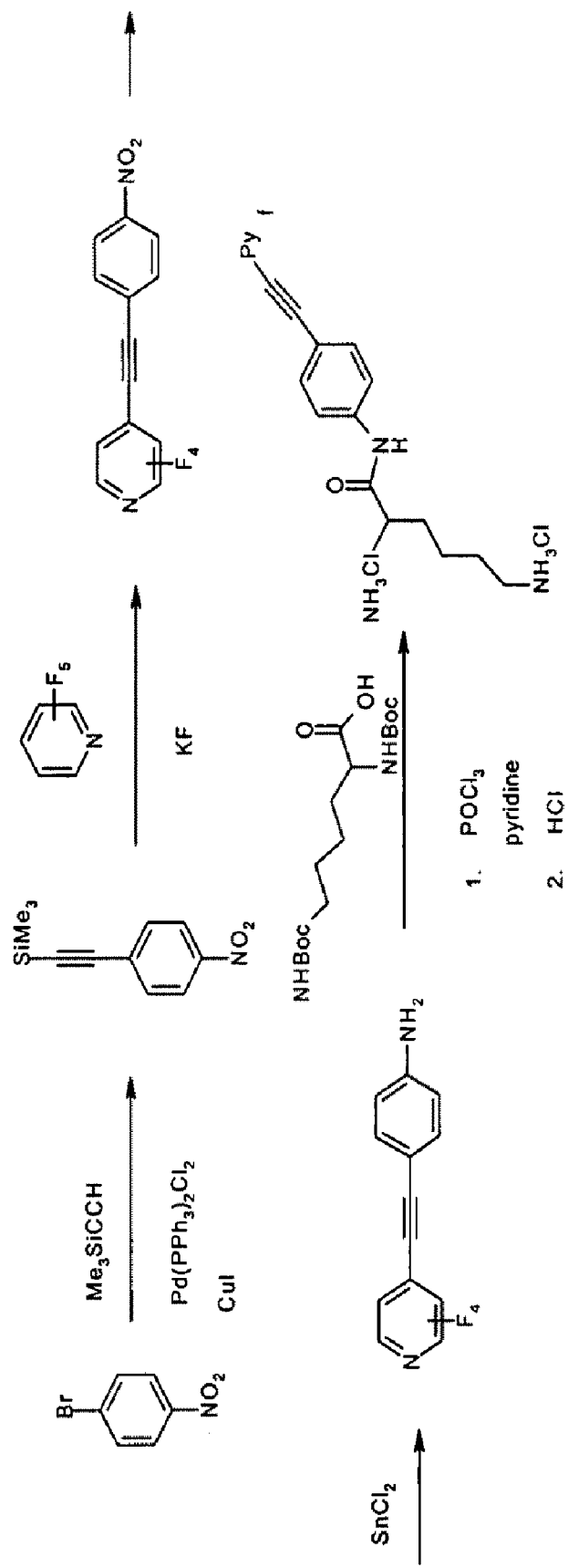
FIG. 6 illustrates the method of synthesizing the lysine-acetylene conjugate 2.

Synthesis of lysine-acetylene conjugate 2: as shown in FIG. 6

4-(Trimethylsilylethynyl)nitrobenzene. A mixture of p-bromonitrobenzene (2.02 g, 10 mmol), bis(triphenylphosphine)palladium(II) chloride (0.2 g, 0.3 mmol), and copper(I) iodide (0.05 g, 0.3 mmol) in 40 ml of N,N-diisopropylamine was degassed by freeze/pump/thaw technique (three times). Trimethylsilylacetylene (1.2 g, 12 mmol) was added and the mixture was refluxed for 12 hours. After removal of amine by rotary evaporation, the residue was dissolved in $CH_2Cl_2$ and washed with water. The organic layer was dried ($Na_2SO_4$), filtered, and rotary evaporated. The residue was purified by column chromatography (EtOAc/hexanes, 1:10) to afford 4-(trimethylsilylethynyl)nitrobenzene (1.53 g, 70%). (Procedure adapted from Takahashi, S; Kuroyama, Y; Sonogashira, K; Hagihara, N. *Synthesis*, 1980, 627.)

4-(2,3,5,6-Tetrafluoropyridin-4-ylethynyl)nitrobenzene. A solution of 4-(2,3,5,6-trimethylsilylethynyl)nitrobenzene (0.95 g, 4.3 mmol) in DMF (10 mL) was added to the mixture of pentafluoropyridine (0.73 g, 4.3 mmol) and CsF(1.0 g, 6.5 mmol, 1.5 eq.) in DMF (10 mL) for 4 h using syringe pump. The reaction mixture was stirred constantly during the addition. Water (20 mL) and dichloromethane (50 mL) were added after the addition was complete. Organic phase was separated, washed with ammonium chloride aqueous solution. Solvent was evaporated. The residue was chromatographed (EtOAc/hexanes, 1:15) to provide 4-(2,3,5,6-tetrafluoropyridin-4-ylethynyl)nitrobenzene as a slightly yellow solid (0.77 g, 60%): mp. 155-158° C.; $^1$H NMR (300 MHz, CDCl$_3$) δ 8.32-8.29 (d, J=9 Hz, 2H), 7.82-7.79 (d, J=9 Hz, 2H). $^{13}$C NMR δ (68 MHz, CDCl$_3$) 148.5, 145 (m), 143 (m), 141 (m), 140 (m), 133.2, 126.9, 123.9, 116 (m), 103.1. $^{19}$F (282 MHz, CDCl$_3$) δ–137.5 (m), –89.6 (m).

4-(2,3,5,6-Tetrafluoropyridin-4-ylethynyl)aniline. A solution of SnCl$_2$ (1.6 g, 8.4 mmol) in THF (5 ml) was slowly (1.5 hours) added to the mixture of 4-(2,3,5,6-tetrafluoropyridynylethynyl)nitrobenzene (0.5 g, 1.7 mmol) and HCl (1 ml) in THF (5 ml). The reaction mixture was stirred at the room temperature for 2 hours. After neutralization with NaOH (1.0; N solution), product was extracted with dichloromethane. Solvent was evaporated and the residue was purified by column chromatography on silica gel using chloroform as the eluent to yield 3,4-bis(tetrafluoropyridinylethynyl)aniline as a yellow solid (0.39 g, 86%): mp. 164-165° C.; $^1$H NMR (300 MHz, CDCl$_3$) δ 7.44-7.42 (d, J=8.7 Hz, 2H), 6.68-6.65 (d, J=8.7 Hz, 2H), 4.04 (broad, 2H). $^{13}$C NMR δ (68 MHz, CD$_3$CN) 152.0, 146 (m), 144 (m), 142 (m), 140 (m), 135.0, 115.1, 110 (m), 107.9, 73 (m). $^{19}$F (282 MHz, CDCl$_3$) δ–136.5 (m), –88.6 (m).

2,6-Diamino-hexanoic acid [4-(2,3,5,6-tetrafluoro-pyridin-4-ylethynyl)-phenyl]-amide Dichloride. Boc$_2$Lys(OH) (1.3 g, 3.7 mmol) and aniline (0.34 g, 3.7 mmol) were dissolved in pyridine (10 mL). The solution was cooled to –20° C. and phosphorus oxychloride (0.5 ml, 5.2 mmol) was added dropwise with vigorous stirring. The reaction mixture was stirred for 1 h at –20° C. and then at room temperature for 10 h. The reaction mixture was quenched with ice/water and anilide was extracted with CH$_2$Cl$_2$. The organic phase was washed with aqueous sodium bicarbonate and saturated aqueous sodium chloride. The organic phase was dried with Na$_2$SO$_4$ and the solvent was evaporated in vacuo. The crude product was subjected to chromatography with CH$_2$Cl$_2$/CH$_3$CN (10: 1) as eluent and desired compound obtained as white solid (1.1 g, 51%): mp. 137-139° C. $^1$H NMR (300 MHz, CDCl$_3$) δ 9.15 (broad, 1H), 7.58-7.55 (d, J=8.4 Hz, 2H), 7.49-7.46 (d, J=8.4 Hz, 2H), 5.42 (broad, 1H) 4.7 (broad, 1H), 4.26 (broad, 1H), 3.12 (broad, 2H), 1.9 (m, 1H), 1.7 (m, 1H), 1.5 (m, 2H), 1.4 (s, 18H). $^{13}$C NMR δ (68 MHz, CDCl$_3$) 171.2, 156.5, 156.3, 145 (m), 143 (m), 142 (m), 140.2, 140 (m), 133.2, 119.3, 117 (m), 115.5, 106.8, 80.7, 79.38, 73 (m), 55.2, 39.6, 31.3, 29.6, 28.4, 28.3, 22.5. $^{19}$F (282 MHz, CDCl$_3$) δ–139.0 (m), –91.0 (m). 0.6 g of this compound was dissolved in THF, and gaseous HCl was passed through that solution for 1 h. The solvent was evaporated, and solid (0.18 g, 40%) was recrystallized from ethanol. Mp. 260-264° (decomp.). $^1$H NMR (300 MHz, DMSO) δ 8.35 (broad, 1H), 7.8-7.82 (d, J=9 Hz, 2H), 7.78 (broad, 1H) 7.72-7.69 (d, J=9 Hz, 2H), 4.04 (broad, 1H), 2.76 (broad, 2H), 1.84 (m, 2H), 1.6 (m, 2H), 1.4 (m, 2H). $^{13}$C NMR δ (68 MHz, CDCl$_3$+CD$_3$OD) 165.9, 144 (m), 143 (m), 141 (m), 140 (m), 139.4, 132.6, 119.2, 115.7, 105.9, 73 (m), 52.9, 38.4, 30.3, 26.0, 21.1. $^{19}$F (282 MHz, CDCl$_3$) δ–140.0 (m), –92.0 (m).

Nucleic Acids

We used an internally $^{32}$P-labeled 54 nt DNA (BW 54s, 5'-TAA TAC GAC TCA CTA TAG GCC CAG GGA AAA CTT GTA AAG GTC TAC CTA TCT *ATT, a $^{32}$P label indicated by asterisk; and identified herein as SEQ ID No:1). This sequence incorporates several isolated guanine (G) nucleotides as well as GG diads, GGG triads, and an AT tract, the latter serving as a natural binding site for a family of lysine-conjugates. We have previously shown that a combination of AT-selectivity of binding and G-selectivity of activation through photoinduced electron transfer (PET) can be used for selective targeting of guanines flanking the AT-tract. See: Breiner, B. and J. C. Schlatterer, S. V. Kovalenko, Nancy L. Greenbaum and I. V. Alabugin in *Angew. Chem. Int. Ed.* 2006, 45, 3666, a scientific paper accessible to the skilled and which is incorporated herein by reference in its entirety.

$^{32}$P-labelling of DNA oligomers for phototriggered damage: The synthesis of BW 54 s was described previously. Id. Aqueous 2 μM dsDNA solution was generated by mixing the appropriate DNA oligomers (see below), incubation at 94° C. for 3 minutes and cooling down to room temperature within 60 minutes. Typically ~1000 cpm were used per experiment. A+G and C+T sequence markers were produced according to the Maxam-Gilbert sequencing protocol (Sambrook, J., E. F. Fritsch and T. Maniatis, 1989, Molecular Cloning: A Laboratory Manual. Cold Spring Harbor Lab. Press, Plainview, N.Y.; a learned treatise known to the skilled and incorporated herein by reference in its entirety) and were loaded on the gels in the lanes labelled A+G and C+T, respectively.

The following oligomers were annealed with BW 54s to generate constructs A-G', which are set forth below:

A:
BW 54 as (SEQ ID NO:2): 5'-AAT AGA TAG GTA GAC CTT TAC AAG TTT TCC CTG GGC CTA TAG TGA GTC GTA TTA

B:
BW 54-x short (SEQ ID NO:3): 5'-AAT AGA TAG GTA GAC CTT T
BW 54-x (SEQ ID NO:4): 5'-pACA AGT TTT CCC TGG GCC TAT AGT GAG TCG TAT TA C:
BW 54-y (SEQ ID NO:5): 5'-pCCT GGG CCT ATA GTG AGT CGT ATT A
BW 54-y short (SEQ ID NO:6): 5'-AAT AGA TAG GTA GAC CTT TAC AAG TTT TC C':
BW 54-y ohne (SEQ ID NO:7): 5'-CCT GGG CCT ATA GTG AGT CGT ATT A
BW 54-y short (SEQ ID NO:8): 5'-AAT AGA TAG GTA GAC CTT TAC AAG TTT TC D:
BW 54-x short-1 (SEQ ID NO:9): 5'-AAT AGA TAG GTA GAC CTTp
BW 54-x (SEQ ID NO:10): 5'-pACA AGT TTT CCC TGG GCC TAT AGT GAG TCG TAT TA E:
BW 54-y (SEQ ID NO:11): 5'-pCCT GGG CCT ATA GTG AGT CGT ATT A
BW 54-y short-1 (SEQ ID NO:12): 5'-AAT AGA TAG GTA GAC CTT TAC AAG TTT Tp E':
BW 54-y ohne (SEQ ID NO:13): 5'-CCT GGG CCT ATA GTG AGT CGT ATT A
BW 54-y short-1 ohne (SEQ ID NO:14): 5'-AAT AGA TAG GTA GAC CTT TAC AAG TTT T F:
BW 54 V (SEQ ID NO:15): 5'-AAT AGA TAG GTA GAC CTT TAC AAG TTT TCC CTG GGC Cp
BW 54 V-1 (SEQ ID NO:16): 5'-pATA GTG AGT CGT ATT A F':
BW 54 V ohne (SEQ ID NO:17): 5'-AAT AGA TAG GTA GAC CTT TAC AAG TTT TCC CTG GGC C
BW 54 V-1 ohne (SEQ ID NO:18): 5'-ATA GTG AGT CGT ATT A G:
BW 54 W (SEQ ID NO:19): 5'-AAT AGA TAG GTA GAC CTT TAp BW 54 W-1 (SEQ ID NO:20): 5'-pAAG TTT TCC CTG GGC CTA TAG TGA GTC GTA TTA G':
BW 54 W ohne (SEQ ID NO:21): 5'-AAT AGA TAG GTA GAC CTT TA
BW 54 W-1 ohne (SEQ ID NO:22): 5'-AAG TTT TCC CTG GGC CTA TAG TGA GTC GTA TTA Cleavage Reactions In a typical reaction, 2.5 L of oligomer-solution (2 M in H2O), 1 L of borate buffer (200 mM) and 1.5 L (33 M) of an aqueous solution of compound 1 were irradiated for the indicated amount of time in a microcentrifuge tube. After irradiation, all samples were evaporated to dryness in vacuo. Samples that were not treated with piperidine were immediately dissolved in loading buffer (80% formamide v/v, 10 mM EDTA, 0.1 mg/ml Xylene cyanol, 1 mg/ml brom phenol blue, 5 mM NaOH). The remaining samples were treated with piperidine (20 L, 90° C., 30 min), evaporated to dryness and co-evaporated with H2O (20 L) twice before dissolving them in loading buffer. The reactions were analyzed using a 12% denaturating (8M urea, 25% formamide) polyacrylamide gel. Electrophoreses were performed at 2000-2500 V and were generally complete after 3-3.5 h. The gels were cooled to ~4° C. and visualized and quantified using a phosphorimaging screen (Molecular Dynamics), and a Storm 860 Scanner (Molecular Dynamics).

Figure 7:
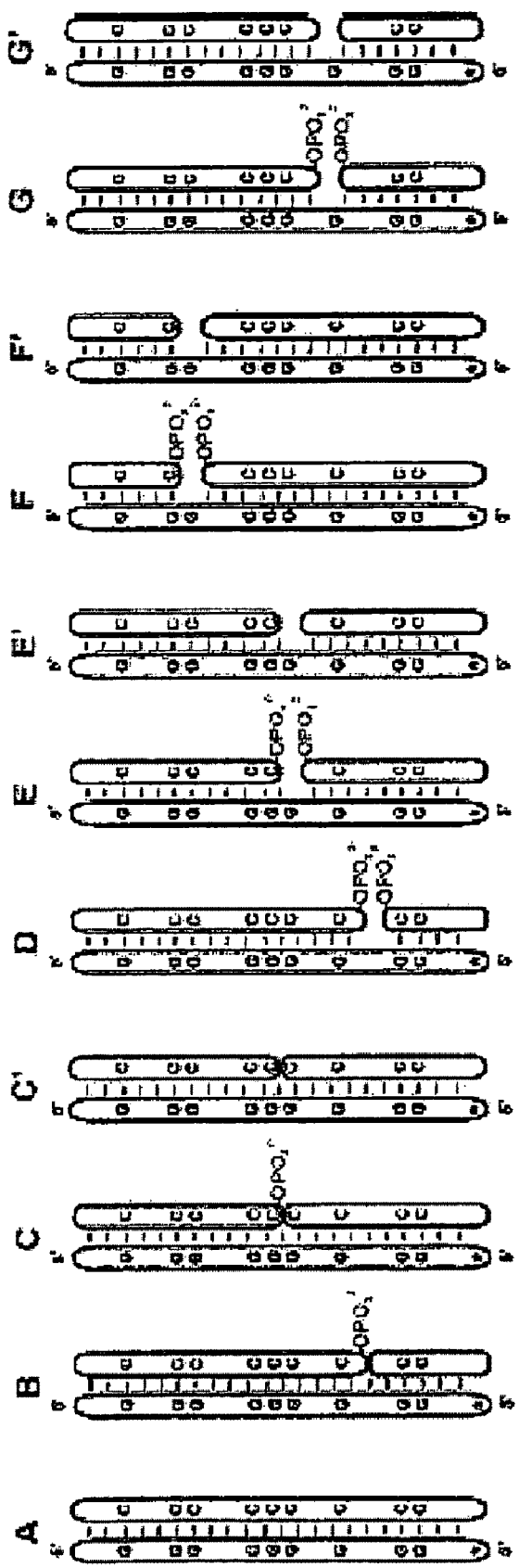
FIG. 7 shows the design of control DNA duplex 54mer and single strand (ss) damage sites, according to an embodiment of the present invention.

By annealing BW 54s with a variety of counterstrands, we built a family of constructs (FIG. 7) inspired by a selection of sites that formed either in the process of chemical damage of DNA or, transiently, during enzymatic processing of DNA. Nicked DNA (constructs B and C) is involved in DNA topological transitions, DNA repair synthesis and DNA replication of the lagging strand. Single nucleotide gaps with 3'- and 5'-phosphorylated ends (constructs D and E) can be formed by AP-lyase activity of DNA glycosylases, or from gaps with 3'-phospholycolate-5'-phosphate ends generated as the result of 4'-H abstraction by natural antibiotics such as bleomycin or by hydroxyl radicals produced by electromagnetic radiation. The structure of the lysine-enediyne conjugate 1 and the lysine-acetylene conjugate 2 are shown in FIG. 4. These compounds are equipped with potent photoactivated "warheads," as they are known by the skilled, and satisfy Lipinski's rule of five for drug design with respect to their molecular weight (<500) and H-bonding ability (not more than 5 donors, not more than 10 acceptors).

Figure 8:
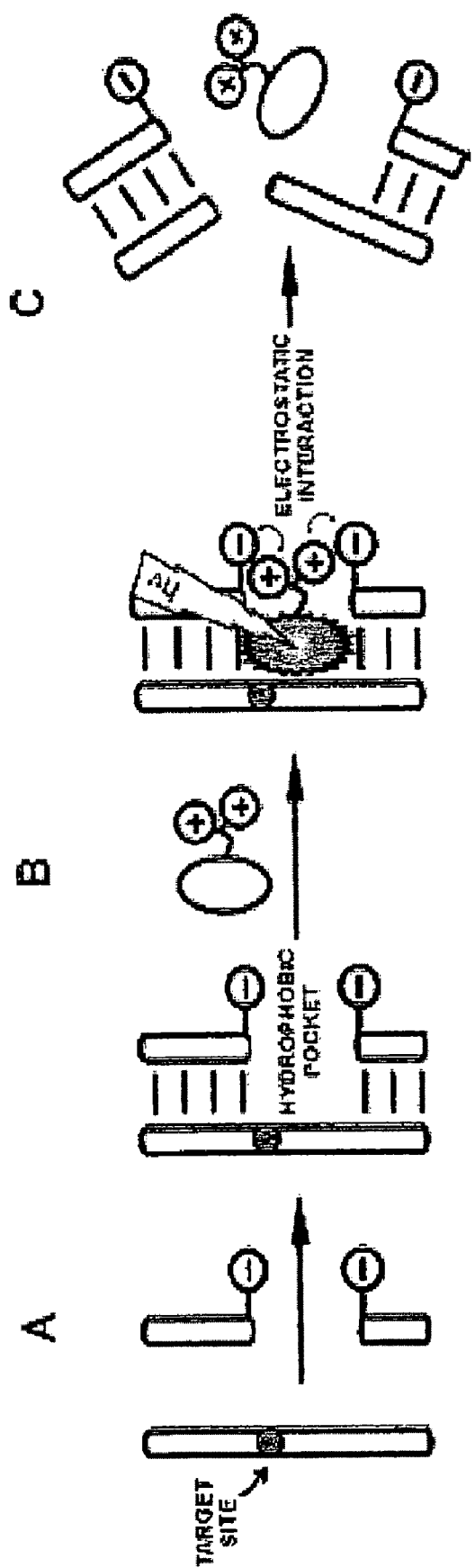
FIG. 8 diagrams a hypothetical mechanism for the present inventive method, showing a diagrammatic view of Scheme 1, where two components are potentially responsible for damage site recognition and subsequent cleavage: 1) formation of a hydrophobic pocket and 2) electrostatic interaction between the additional negative charges due to the presence of terminal phosphate moieties at the negatively charged DNA backbone ((−) signs) and the protonated amines of lysine moiety ((+) charges). A. Annealing process that positions recognition site opposite the target at the original single strand oligonucleotide. B. Recognition of the target site by lysine conjugates. C. Sequence-selective photochemical conversion of single stranded DNA cleavage into double stranded cleavage.
Figure 9:
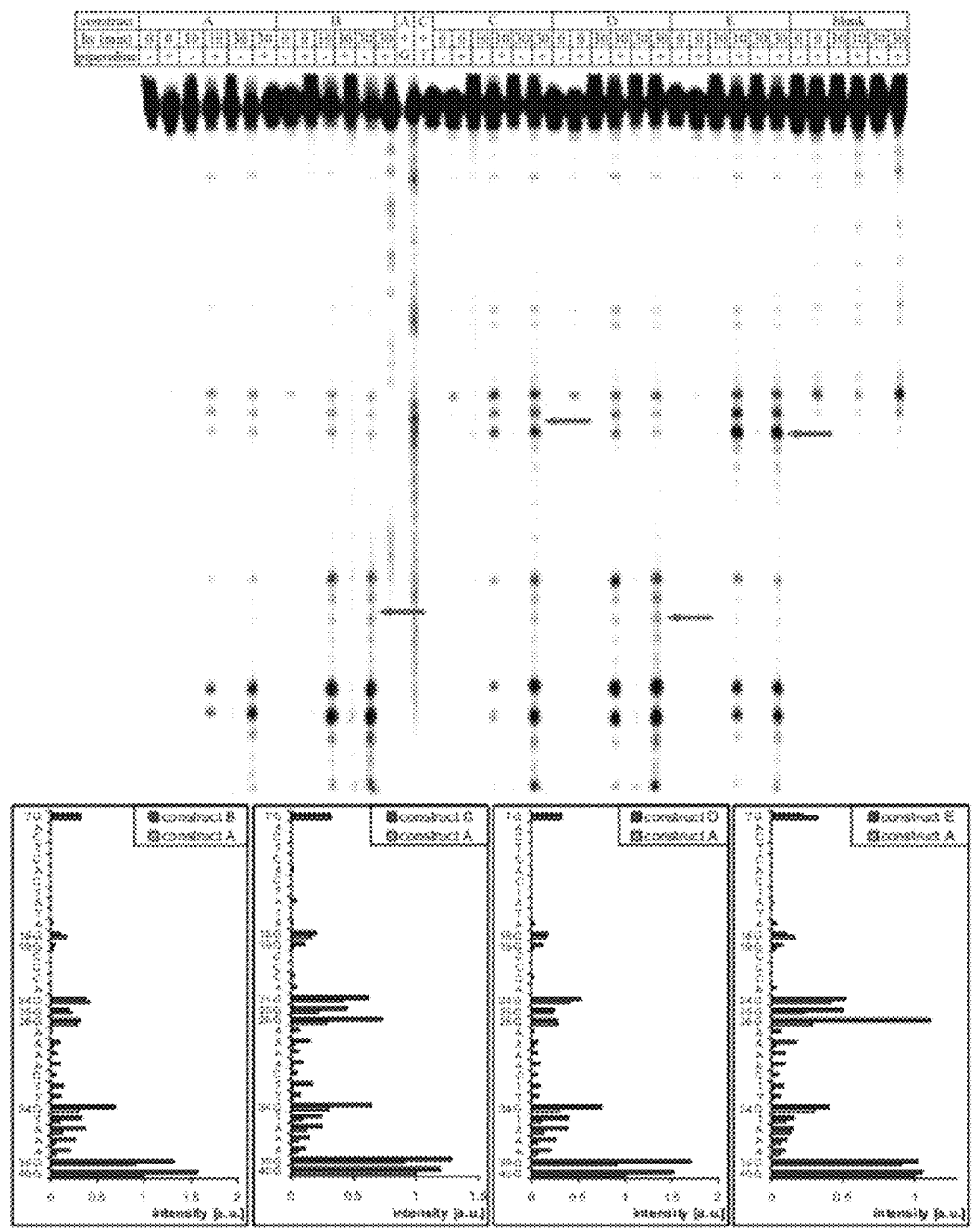
FIG. 9 is a comparison between the intact DNA duplex A and constructs B, C, D, and E.; the constructs (0.2 μM) were irradiated in presence of compound 1 (10 μM) in borate buffer (pH 7.6); top: autoradiogram of PAGE analysis; the arrows show the position of the target site; bottom: histograms showing the quantified cleavage data, normalized relative to the largest peak in construct A.

While not intending to be bound by this particular explanation of the invention's method of operation, we envisioned that the hydrophobic "warheads" bind to the nucleic acid to occupy a hydrophobic pocket created by the omission of a base, whereas the mono- or bis-protonated hydrophilic lysine residue will additionally experience strong coulombic attraction towards a terminal phosphate mono- or di-anion, as shown generally in FIG. 8.

Four sets of target sites were constructed within BW 54. The first site was chosen to be opposite $G_{26}$ of the $G_{24}G_{25}G_{26}$ triad, which is a natural (but minor) cleavage site for the reaction of this conjugate with undamaged duplex DNA. The second one was opposite $G_{19}$ of the $G_{18}G_{19}$ diad, which is not part of a natural binding site. The third and fourth sites were opposite $G_{34}$ and $A_{36}$, respectively. These sites were chosen to ascertain whether it was possible to target a single G site or other nucleotides. We wanted to know whether the damage remains localized or propagates to the nearby $G_{34}$ and $G_{39}G_{40}$ by the hole-hopping mechanism, which may be important when electron transfer from DNA is involved in the "warhead" activation step. We irradiated the constructs in presence of compound 1 or 2 (10 μM), and analyzed the resulting cleavage patterns by denaturing PAGE, followed by phosphorimaging and quantification with SAFA software (Das, R., A. Laederach, S. Pearlman, D. Herschlag and R. Altman; *RNA* 2005, 11, 344; a scientific paper accessible to the skilled and incorporated herein by reference in its entirety). Comparisons of construct cleavages are shown in FIGS. 9-14.

All constructs showed enhanced cleavage at the respective target sites. Constructs with a "gap", an unpaired base in the target strand, displayed the greatest effect, especially when the target was within the natural AT-rich binding site (D, E, E', G, G'). Gaps outside of the AT-tract were less effective (constructs F and F') and showed migration of damage away from the target $G_{19}$ base not only to the adjacent $G_{18}$ but also a more remote G, site. Interestingly, the migration of damage was unidirectional and no enhancement is observed at the $G_{24}G_{25}G_{26}$ triad. In all cases, however, cleavage at the site targeted by the construct was clearly enhanced. In the case of constructs without the "gap" (B, C, C'), the enhancement was also evident, albeit to a smaller degree than in the "gapped" constructs.

Figure 10:
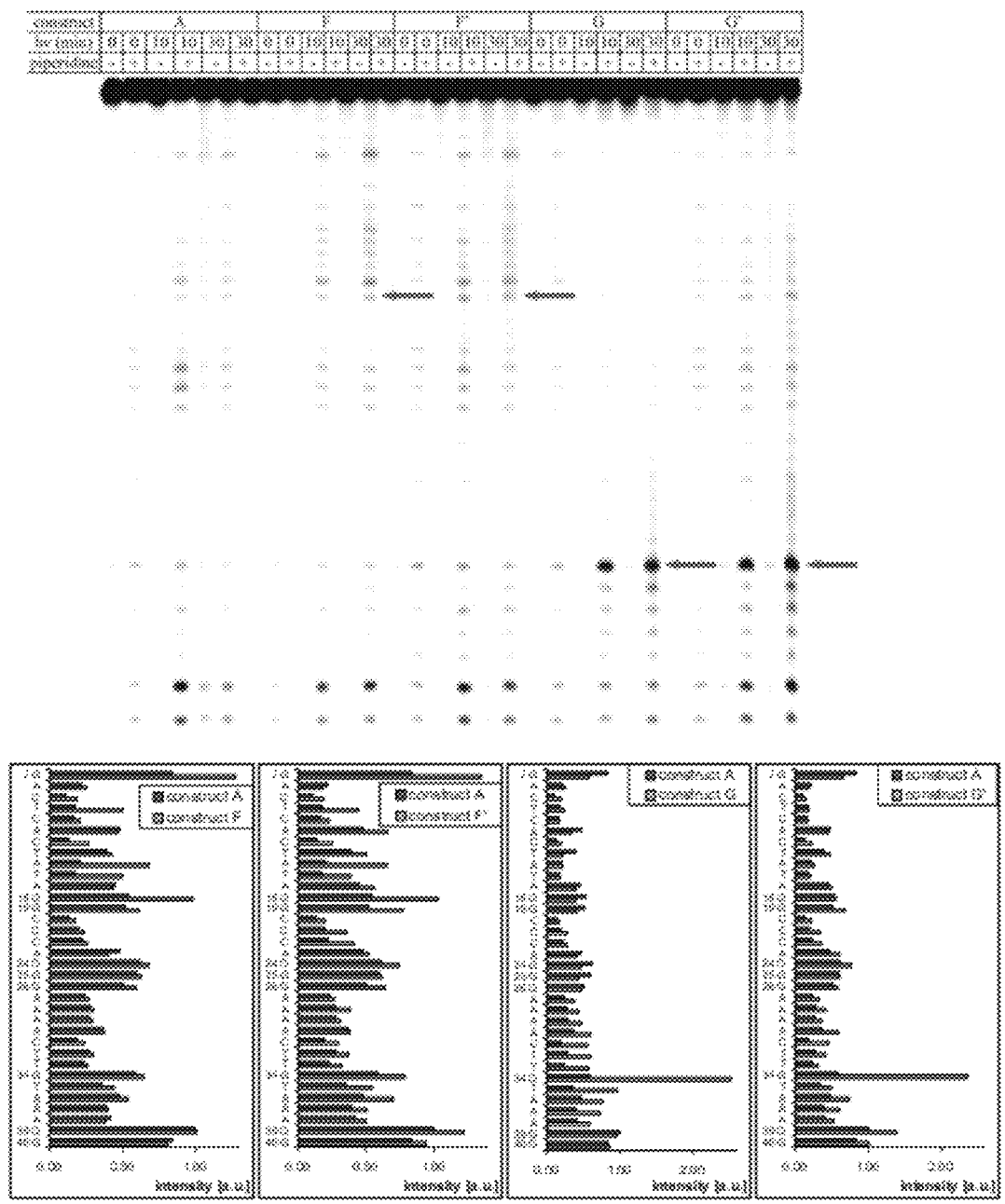
FIG. 10 illustrates a comparison between DNA construct A and constructs F, F', G, and G'; the constructs (1 μM) were irradiated in presence of compound 1 (10 μM) in borate buffer (pH 7.6); the arrows show the position of the target site; top: autoradiogram of PAGE analysis; bottom: histograms showing the quantified cleavage data, normalized relative to the largest peak in construct A.
Figure 11:
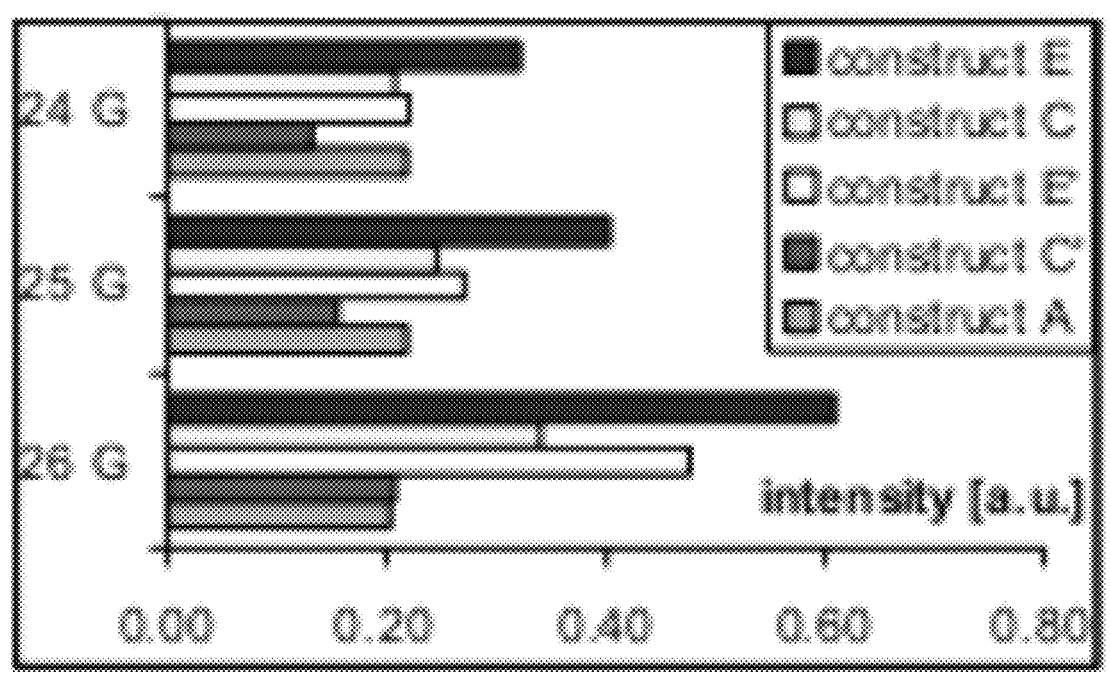
FIG. 11 displays histograms showing the amount of frank cleavage at the $G_{24}G_{25}G_{26}$ triad in various constructs under identical conditions; intensities are relative to the largest peak in construct A. E and E' correspond to gapped constructs with and without terminal phosphate groups.
Figure 12:
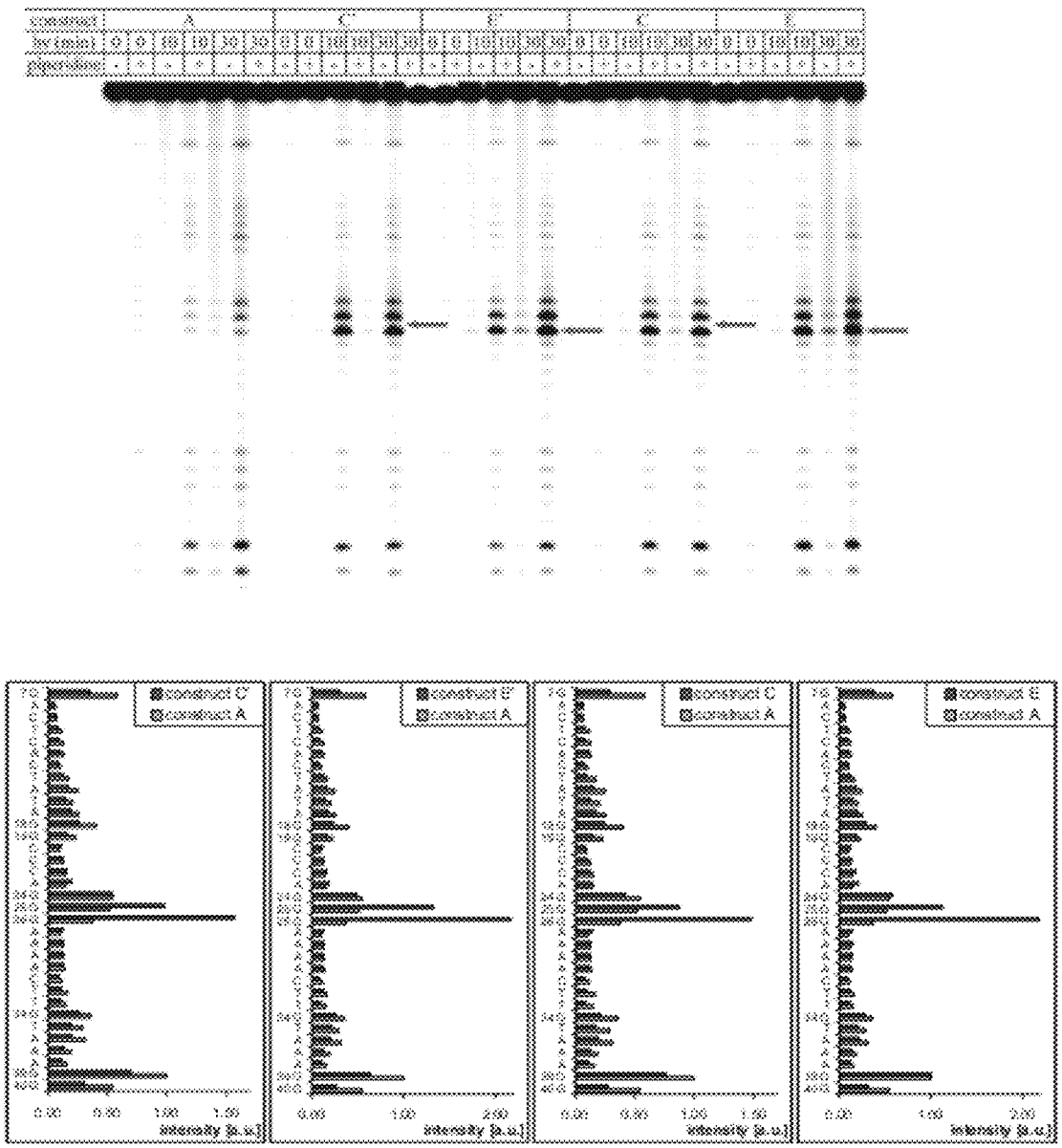
FIG. 12 is a comparison between DNA construct A and constructs C', E', C, and E; the constructs (1 M) were irradiated in presence of compound 1 (10 M) in borate buffer (pH 7.6); top: autoradiogram of PAGE analysis, the arrows show the position of the target site.; bottom: histograms showing quantified cleavage data, normalized relative to the largest peak in construct A.
Figure 13:
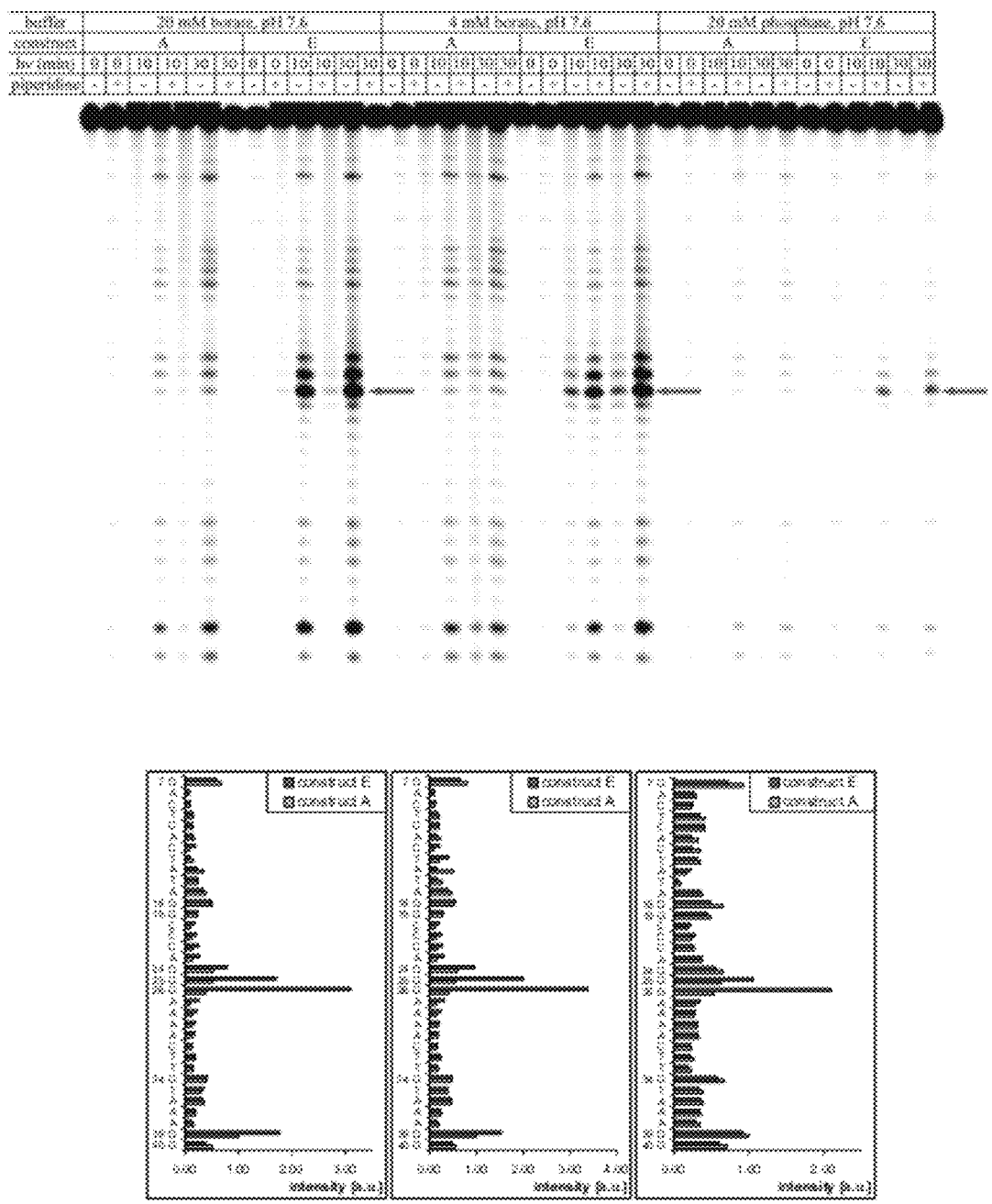
FIG. 13 shows a comparison between DNA constructs A and E in different buffer conditions; the constructs (1 M) were irradiated in presence of compound 1 (10 M) in left: borate buffer (pH 7.6, 20 mM); middle: borate buffer (pH 7.6, 4 mM); right: phosphate buffer (pH 7.6, 20 mM); top: autoradiogram of PAGE analysis, the arrows show the position of the target site; bottom: histograms showing the quantified cleavage data, normalized relative to the largest peak in construct A.
Figure 14:
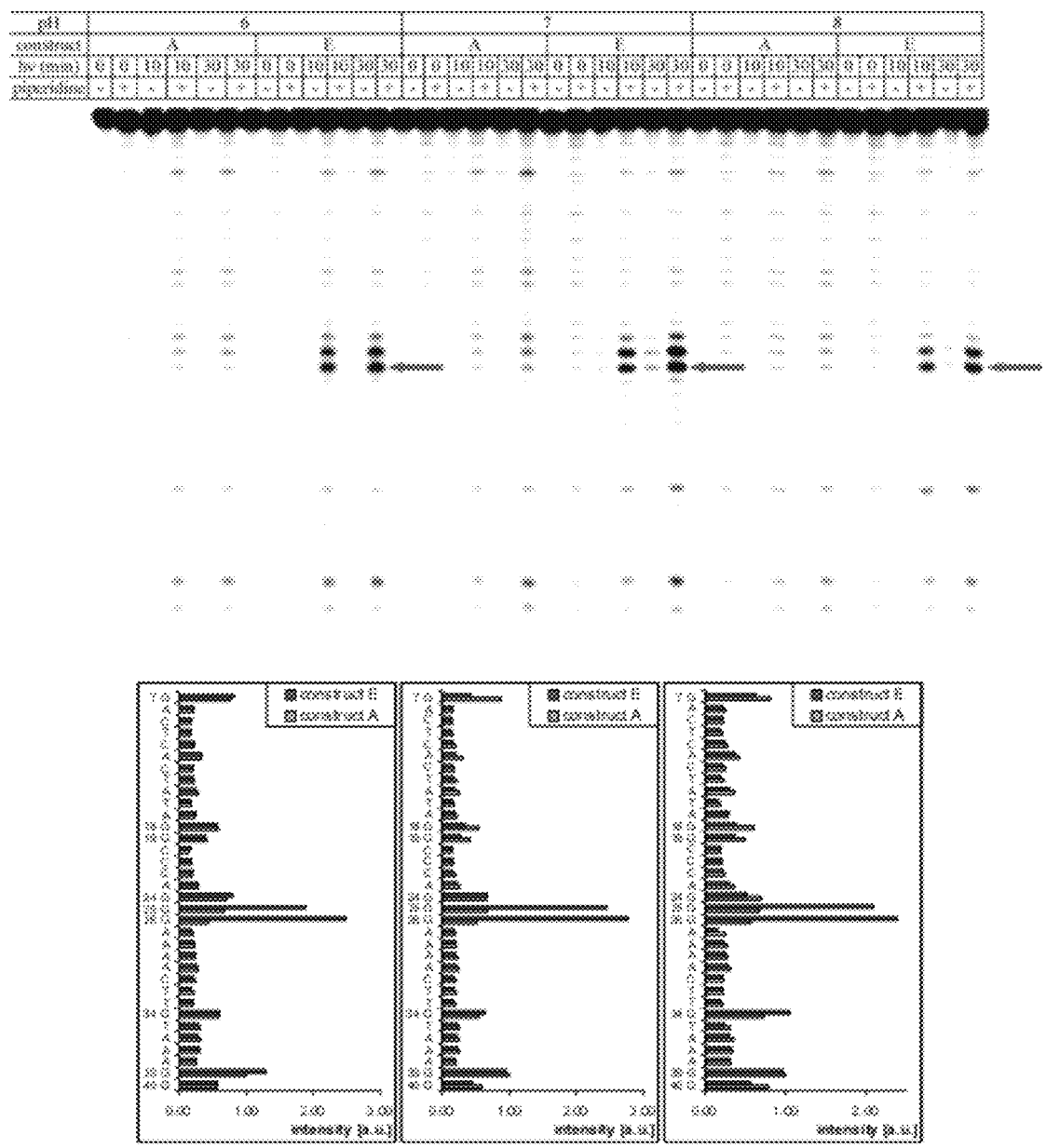
FIG. 14 is a comparison between DNA constructs A and E in different buffer conditions; the constructs (1 M) were irradiated in presence of compound 2 (10 M) in phosphate buffer; left: pH 6; middle: pH 7; right: pH 8; top: autoradiogram of PAGE analysis; the arrows show the position of the target site; bottom: histograms showing the quantified cleavage data, normalized relative to the largest peak in construct A.

In the cases where the target site was not at a (multiple) G (constructs B and D), the cleavage was distributed over an array of bases terminated by the nearest G. Both the single $G_{34}$ and the $G_{39}G_{40}$ doublet showed increased cleavage, but also the whole NT area in between these two sites displayed more damage relative to the duplex DNA. Remarkably, once the target site is moved only two bases to $G_{34}$ (constructs G and G'), all the damage enhancement is localized at that site, resulting in amplification by a factor of 5-6 on what used to be a minor cleavage site in the ds construct (FIG. 10). Localization of damage at a single G in the presence of nearby (G)n sites illustrates that dissipation of the damage by hole-hopping does not interfere. In order to compare the different types of constructs (with/without gap, with/without phosphate group(s)), we compared constructs C, C', E, and E' directly, again using the "undamaged" double stranded construct A as reference.

Enhancement of piperidine-induced cleavage is identical within each pair of constructs with (E and E') and without a gap (C and C'), suggesting that, unlike the gap, phosphate groups apparently have no influence at the oxidative piperidine-induced DNA cleavage. On the other hand, frank photocleavage induced by our compounds, which may occur due to direct H-abstraction by radical species, is clearly enhanced both by the presence of phosphate groups and by the hydrophobic pocket (see FIG. 11).

In order to understand the role of the phosphate groups in the recognition of lysine-conjugates, we also varied the buffer conditions. The directing effect, as well as the reactivity, is much more pronounced in borate buffer than it is in phosphate buffer. While we observe an enhancement by a factor of approximately eight in borate buffer, the directing efficiency of the target site is reduced by ~50% in 20 mM phosphate buffer. These findings suggest that recognition between the ammonium groups of lysine and phosphates of the DNA does contribute to the directing effect and that this contribution decreases upon "dilution" with the external phosphate moieties. Nevertheless, even in presence of a 4000-20000 molar excess of phosphate, the directing effect is still present, suggesting the robustness of these recognition patterns.

Both the robustness and the versatility of DNA damage recognition are further illustrated by reactivity of another lysine conjugate (according to formula 2) over a wider range of conditions. Differences in selectivity are minimal for experimental results for pH 6, pH 7, and pH 8, and cleavage at the target site is amplified by a factor of 5-6, even in the presence of phosphate buffer. These experiments show that the effect is general and can be used with a variety of DNA-cleaving agents under a variety of conditions.

The directing effect of ss damage sites provides a new explanation for the unusually high ratios of double strand to single strand (ds/ss) cleavage of plasmid DNA by enediyne-lysine conjugates, where statistical evidence based on the Poisson distribution suggested a dramatic increase in the amount of ds cleavage compared to that expected from a combination of random ss cleavages. Although statistical evidence does not differentiate between the true ds cleavage and this alternative scenario, the possibility of directing a second attack through recognition of the initial ss cleavage points to a new strategy in the design of highly reactive ds DNA cleaving agents.

Accordingly, the present invention shows that it is possible for small molecules (MW<500) to recognize damage sites in one strand of double stranded DNA, and to use this recognition to direct subsequent damage to a specified location at the counterstrand, thus converting ss cleavage to ds cleavage. While such recognition is known for enzymes and some large natural products, the present invention demonstrates that the underlying working pattern can be simulated with compounds that are smaller than enzymes by at least two orders of magnitude.

Having read the disclosure provided by the inventors, those skilled in the art will appreciate that the invention includes a number of embodiments, including a process of forming a double strand cleavage in DNA. This process comprises providing a reaction mixture containing double stranded DNA having a break in a first strand defining a target site in a second strand. The break defines a target site on the unbroken strand. The break can be created by photochemical or chemical cleavage of an intact duplex or can be created artificially by annealing a single nucleotide strand with one or more shorter counterstrands. The method continues by adding to the reaction mixture a photoreactive lysine conjugate selected from lysine-enediyne conjugate according to formula I, a lysine-acetylene conjugate according to formula II and combinations thereof, for a time sufficient for the lysine conjugate to bind to the DNA adjacent the target site. Finally, the method calls for irradiating the reaction mixture with electromagnetic radiation sufficient to photoactivate the lysine conjugate to cleave the second strand adjacent the target site.

Another preferred embodiment of the invention is a process for cleaving double stranded DNA, the process comprising reacting double stranded DNA containing a target site adjacent a nick or gap in a first strand with a photoreactive lysine enediyne conjugate according to formula I or a lysine acetylene conjugate according to formula II, and irradiating the mixture at a wavelength effective for causing photoactivation of the conjugate to thereby cleave a second strand of the DNA adjacent the target site.

Yet an additional preferred embodiment of the invention is a method for site-directed cleavage of a nucleic acid strand. This method comprises synthesizing a complementary counterstrand bearing a terminal phosphate group. The method then proceeds by annealing the nucleic acid strand and the counterstrand so that the terminal phosphate on the counterstrand is opposite one or more guanosines on the nucleic acid strand. A reaction is started by mixing the annealed strands with a photoreactive phosphate-detecting ligand conjugate. Finally, the reaction mixture is irradiated at a wavelength effective for photoactivating the conjugate to cleave the nucleic acid strand at the site of the one or more guanosines.

A further preferred method of the invention provides for site-directed cleavage of a nucleic acid strand. This method comprises synthesizing a counterstrand complementary to a predetermined region of the nucleic acid strand, the counterstrand bearing a terminal phosphate group. The method then calls for annealing the counterstrand with the predetermined region of the nucleic acid strand so that the terminal phosphate group on the counterstrand is approximately opposite a selected target site on the nucleic acid strand. The annealed strands are then contacted with a photoreactive ligand conjugate effective for complexing with the counterstrand at the terminal phosphate group. Lastly, the method ends after irradiating the complex at a wavelength effective for photoactivating the conjugate to cleave the nucleic acid strand at the selected target site.

Accordingly, in the drawings and specification, there have been disclosed typical preferred embodiments of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A purified photoreactive lysine-enediyne conjugate according to formula 1 in FIG. 4.

2. A purified photoreactive lysine-acetylene conjugate according to formula 2 in FIG. 4.

3. A conjugate comprising an amino acid ligand electrostatically linked to a terminal phosphate group of a nucleic acid sequence and covalently linked with a photoreactive alkyne molecule.

4. A conjugate comprising a phosphate detecting ligand electrostatically linked to a terminal phosphate group of a nucleic acid sequence and covalently linked with a photoreactive alkyne molecule.

* * * * *

SEQUENCE LISTING

<160> NUMBER OF SEQ ID NOS: 22

<210> SEQ ID NO 1
<211> LENGTH: 54
<212> TYPE: DNA
<213> ORGANISM: Artificial
<220> FEATURE:
<223> OTHER INFORMATION: internally P-32 labelled 54 nt sequence

<400> SEQUENCE: 1
taatacgact cactataggc ccagggaaaa cttgtaaagg tctacctatc tatt            54

<210> SEQ ID NO 2
<211> LENGTH: 54
<212> TYPE: DNA
<213> ORGANISM: Artificial
<220> FEATURE:
<223> OTHER INFORMATION: oligomer annealed with SEQ ID NO:1 to generate -continued construct

<400> SEQUENCE: 2
aatagatagg tagaccttta caagttttcc ctgggcctat agtgagtcgt atta        54

<210> SEQ ID NO 3
<211> LENGTH: 19
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 3
aatagatagg tagaccttt                                               19

<210> SEQ ID NO 4
<211> LENGTH: 35
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 4
acaagttttc cctgggccta tagtgagtcg tatta                             35

<210> SEQ ID NO 5
<211> LENGTH: 25
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 5
cctgggccta tagtgagtcg tatta                                        25

<210> SEQ ID NO 6
<211> LENGTH: 29
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 6
aatagatagg tagaccttta caagttttc                                    29

<210> SEQ ID NO 7
<211> LENGTH: 25
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 7
cctgggccta tagtgagtcg tatta                                        25

<210> SEQ ID NO 8
<211> LENGTH: 29
<212> TYPE: DNA
<213> ORGANISM: Artificial
<220> FEATURE:
<223> OTHER INFORMATION: oligomer annealed with SEQ ID NO:1 to generate
      construct

```
<400> SEQUENCE: 8
aatagatagg tagacccttta caagttttc                              29

<210> SEQ ID NO 9
<211> LENGTH: 18
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 9
aatagatagg tagacctt                                           18

<210> SEQ ID NO 10
<211> LENGTH: 35
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 10
acaagttttc cctgggccta tagtgagtcg tatta                        35

<210> SEQ ID NO 11
<211> LENGTH: 25
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 11
cctgggccta tagtgagtcg tatta                                   25

<210> SEQ ID NO 12
<211> LENGTH: 28
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 12
aatagatagg tagacccttta caagtttt                               28

<210> SEQ ID NO 13
<211> LENGTH: 25
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 13
cctgggccta tagtgagtcg tatta                                   25

<210> SEQ ID NO 14
<211> LENGTH: 28
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 14
```
aatagatagg tagacctttta caagtttt                                    28

<210> SEQ ID NO 15
<211> LENGTH: 37
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 15
aatagatagg tagacctttta caagttttcc ctgggcc                          37

<210> SEQ ID NO 16
<211> LENGTH: 16
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 16
atagtgagtc gtatta                                                  16

<210> SEQ ID NO 17
<211> LENGTH: 37
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 17
aatagatagg tagacctttta caagttttcc ctgggcc                          37

<210> SEQ ID NO 18
<211> LENGTH: 16
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 18
atagtgagtc gtatta                                                  16

<210> SEQ ID NO 19
<211> LENGTH: 20
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 19
aatagatagg tagaccttta                                              20

<210> SEQ ID NO 20
<211> LENGTH: 33
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 20
aagttttccc tgggcctata gtgagtcgta tta                               33

```
<210> SEQ ID NO 21
<211> LENGTH: 20
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 21
aatagatagg tagacccttta                                                   20

<210> SEQ ID NO 22
<211> LENGTH: 33
<212> TYPE: DNA
<213> ORGANISM: Artificial
<220> FEATURE:
<223> OTHER INFORMATION: oligomer annealed with SEQ ID NO:1 to generate
      construct

<400> SEQUENCE: 22
aagttttccc tgggcctata gtgagtcgta tta                                     33
```